United States Patent
Mouri et al.

(10) Patent No.: US 6,730,418 B2
(45) Date of Patent: May 4, 2004

(54) QUINOLINE DERIVATIVES AND ORGANIC ELECTROLUMINESCENT DEVICES

(75) Inventors: Makoto Mouri, Aichi (JP); Hisato Takeuchi, Aichi (JP); Hiromitsu Tanaka, Aichi (JP); Tomohiko Mori, Aichi (JP); Masahiko Ishii, Aichi (JP); Koji Noda, Aichi (JP); Shizuo Tokito, Kawasaki (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 0 days.

(21) Appl. No.: 10/149,745

(22) PCT Filed: Dec. 13, 2000

(86) PCT No.: PCT/JP00/08790

§ 371 (c)(1),
(2), (4) Date: Jun. 13, 2002

(87) PCT Pub. No.: WO01/42218

PCT Pub. Date: Jun. 14, 2001

(65) Prior Publication Data

US 2003/0012980 A1 Jan. 16, 2003

(30) Foreign Application Priority Data

Dec. 13, 1999 (JP) .............................. 11-353703

(51) Int. Cl.[7] .................. H05B 33/14; C07D 453/02
(52) U.S. Cl. .................. 428/690; 428/704; 428/917; 313/504; 313/506; 252/301.16; 252/301.26; 257/40; 257/103; 546/112; 546/134; 546/135; 546/268.1
(58) Field of Search .................. 428/690, 704, 428/917; 313/504, 506; 252/301.16, 301.26; 257/40, 103; 546/112, 134, 135, 268.1

(56) References Cited

U.S. PATENT DOCUMENTS

| | | |
|---|---|---|
| 5,077,142 A | 12/1991 | Sakon et al. |
| 5,121,029 A | 6/1992 | Hosokawa et al. |
| 5,150,006 A | 9/1992 | VanSlyke et al. |
| 5,151,629 A | 9/1992 | VanSlyke |
| 5,821,002 A | 10/1998 | Ohnishi et al. |
| 5,948,782 A | 9/1999 | Sohda et al. |

FOREIGN PATENT DOCUMENTS

| | | |
|---|---|---|
| EP | 763965 | 3/1997 |
| JP | 04-103571 | 4/1992 |
| JP | 07-150137 | 6/1995 |
| JP | 7288184 | 10/1995 |
| JP | 9296166 | 11/1997 |
| JP | 09-328472 | 12/1997 |
| JP | 2809473 | 7/1998 |
| JP | 3076603 | 6/2000 |
| JP | 2000303066 | 10/2000 |
| WO | 97/23200 | 7/1997 |

OTHER PUBLICATIONS

Jose Barluenga et al.: "Lewis acid–catalyzed cyclization of 3–amino–2–alkenimines.Synthesis of quinolines" Synthesis, No. 1, pp. 82–84 1987, (No Month).

Robert E. Pratt et al.: "Quinoline syntheses by reaction of hydrazoic acid with alpha, beta–disubstituted cis–chalcones(1)" J. Heterocycl. Chem., vol. 7, No. 5, pp. 1051–1055 Oct. 1970.

*Primary Examiner*—Deborah Jones
*Assistant Examiner*—Ling Xu
(74) *Attorney, Agent, or Firm*—Oblon, Spivak, McClelland, Maier & Neustadt, P.C.

(57) ABSTRACT

Quinoline derivatives represented by formula (1) wherein two or more of substituents $R_1$ to $R_7$ are each a group of formula (2). In general formula (2), Q is a carbo- or hetero-aryl group; and the number (n) of double bonds is preferably 1 to 3. Use of such derivatives in an organic EL device provided with a layer of an organic compound and two electrodes sandwiching the layer as the organic compound gives devices emitting yellow to red light with high brightness and high efficiency. Further, doping a hole transport layer with such derivatives realizes organic EL devices capable of emitting lights of resultant colors (e.g., white) composed of lights from light-emitting and hole transport layers.

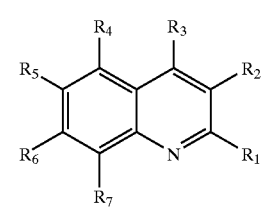

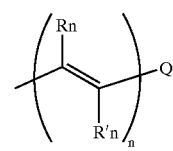

22 Claims, No Drawings

QUINOLINE DERIVATIVES AND ORGANIC ELECTROLUMINESCENT DEVICES

TECHNICAL FIELD

The present invention relates to an organic compound useful as a light emitting material for an organic electroluminescence element (hereinafter referred to as an "organic EL element") and a light emitting material for other electronic device materials or the like, and to an element employing such organic compound.

BACKGROUND ART

Organic EL elements are constructed by layering, on a transparent glass substrate, a transparent first electrode (for example, ITO), an organic compound layer which includes an organic compound having strong fluorescence, and a metal (for example, Mg) second electrode in that order.

The organic layer has, for example, a three-layer structure in which a layer of molecules having a hole transport function, a layer of molecules having an emissive function, and a layer of molecules having an electron transport function are layered in that order, and emits light when an electric field is applied to the pair of electrodes. In other words, when holes are injected from the first electrode and electrons are injected from the second electrode, the injected holes and electrons move through the hole transport functional molecule layer, the emissive functional molecule layer, and the electron transport functional molecule layer of the organic layer, such that the holes and electrons collide, recombine, and disappear. The energy generated by there combination is used for producing exited states of the emissive molecules and fluorescence is emitted from the organic EL element.

In such an organic EL element, an aluminum quinolinol complex ($Alq_3$) represented by a chemical formula (3),

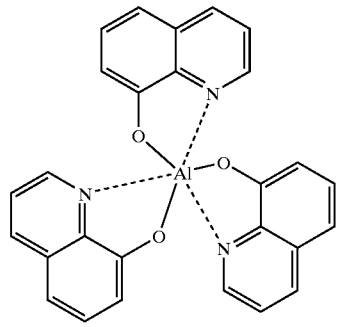

(3)

is well known as a light emitting material having a quinoline ring. This compound is obtained by substituting a hydroxy group into the quinoline ring to form a complex with aluminum and emits a green light.

As a red light emitting material for an organic EL element, a phthalocyanine derivative as disclosed in Japanese Patent Laid-Open Publication No. Hei 7-288184 and a porphyrin derivative as disclosed in Japanese Patent Laid-Open Publication No. Hei 9-296166 are known.

Because all of the known light emitting materials having the quinoline ring such as $Alq_3$ have a short conjugate system, light emitting function has so far been obtained only in the blue~green range. To realize a color organic EL element, it is necessary to obtain a compound which emits light with sufficient characteristics for other colors, specifically those in the yellow~red range.

On the other hand, although the phthalocyanine derivative and porphyrin derivative as described above have a red light emitting function, they do not have sufficient luminance nor sufficient endurance, and, thus, do not satisfy all the requirements desired for applications such as in an organic EL element.

The present invention was conceived to solve the problem described above, and one object of the present invention is to provide a novel organic compound having superior stability and light emitting luminance characteristic and having light emitting function in yellow~red range, and an organic EL element which employs such organic compound.

DISCLOSURE OF INVENTION

In order to achieve at least the object described above, according to the present invention, there is provided a quinoline derivative compound represented by a chemical formula (1),

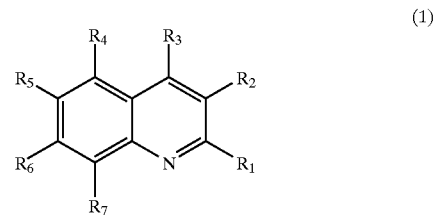

(1)

wherein at least two of the substituents $R_1$~$R_7$ in the chemical formula (1) have a structure represented by a chemical formula (2),

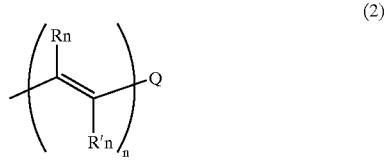

(2)

where Q in the chemical formula (2) is an arbitrary functional group.

In the novel organic compound, at least two substituents having a double bond in the structural formula (chemical formula (2)) are introduced as substituents for the quinoline ring (chemical formula (1)). Because of this, the compound has a structure in which the conjugate system is long and the energy difference between the excited state and the ground state of the compound is small and, thus, light emission function in the yellow~red range can be obtained.

According to another aspect of the present invention, it is preferable that, in the organic compound represented by the chemical formula (1), at least one of the substituents $R_1$~$R_7$ other than the substituents having a structure represented by the chemical formula (2) is an electron attracting substituent.

By introducing an electron attracting substituent as a substituent in the quinoline ring, the fluorescence quantum yield of the compound can be improved and, as a result, a light emitting material which can emit light at higher luminance and higher efficiency can be obtained.

According to another aspect of the present invention, it is preferable that, in the organic compound, Q in chemical formula (2) is an aromatic group having carbon or aheteroatomin the skeleton of the ring and at least one of the substituents $R_Q$ of the aromatic group Q is an electron donating substituent.

By using a stable aromatic group as Q, it is possible to prevent reactions of the double bonds in the chemical formula (2) and thereby improve the stability as a compound. Furthermore, by using at least one electron donating substituent for the substituents $R_Q$, the fluorescence quantum yield of the overall compound represented by the chemical formula (1) can be improved. In particular, it is preferable that an electron attracting group is introduced to at least one of the substituents $R_1$~$R_7$ of the quinoline ring and an electron donating group is introduced as the substituent $R_Q$ of Q. More preferably, a cyano group is used for the subsituent $R_3$ and a p-aminophenyl group is used for the substituent Q. With such a structure, the fluorescence quantum yield of the compound is further improved, and a light emitting material having even higher luminance and higher efficiency can be obtained.

According to another aspect of the present invention, it is preferable that, in the organic compound, the number n of the double bonds in the chemical formula (2) be, for example, at least 2 or no more than 5, or it is also preferable that the number n of the double bonds in the chemical formula (2) be in the range of 1~3.

When the value of n is in the range of 1~3 or 2 or greater, a highly stable compound can be obtained which allows for improvements in the endurance of an element when the compound is used, for example, in an organic compound layer of an organic EL element, as will be described below.

According to another aspect of the present invention, it is preferable that the substituents $R_n$ and $R'_n$ in the chemical formula (2) are cyclized. Through the cyclization, free rotation which is normally generated in a vinyl group represented by the chemical formula (2) can be blocked, and the link in the conjugated system can be maintained. Moreover, separation of the n-bonds within the molecule and alteration of the molecular shape can also be prevented, allowing for improvement in the endurance or the like of the molecule.

According to another aspect of the present invention, there is provided an organic electroluminescence element wherein an organic compound layer which includes an emissive layer is formed between two electrodes, and the organic compound described above, that is, an organic compound represented by the chemical formula (1) and having at least two of the substituents $R_1$~$R_7$ substituted by a substituent represented by the chemical formula (2), is used for the organic compound layer.

As described above, because the organic compound according to the present invention has a light emitting characteristic in the yellow~red range, by using the organic compound as the material for the organic compound layer, in particular, for the emissive layer, of the organic EL element, an organic EL element having high luminance, high efficiency, and high stability can be obtained.

According to another aspect of the present invention, it is preferable that, in the organic electroluminescence element, the organic compound layer comprises a hole transport layer and an emissive layer, and any one of the quinoline derivative compounds described above is doped into the hole transport layer.

According to another aspect of the present invention, there is provided an organic electroluminescence element wherein an organic compound layer which includes an emissive layer is formed between two electrodes, the organic compound layer comprises a blue emissive layer and a hole transport layer doped with any one of the quinoline derivative compounds as described above, and the organic electroluminescence element emits white light.

As described above, the quinoline derivative compound of the present invention not only demonstrates light emission characteristic of yellow~red range when used alone, but also produces a light in a similar wavelength range in a hole transport layer when the quinoline derivative compound is doped to the hole transport layer. Therefore, in an organic EL element, light can be emitted having a color determined by the synthesis of the light from the emissive layer and the light from the hole transport layer. For example, by using a blue light emitting material for the emissive layer and the quinoline derivative compound according to the present invention as the doping material of the hole transport layer, it is possible to obtain a white light emitting organic EL element through the synthesis of the blue light from the blue emissive layer and the light in the orange~red range from the hole transport layer. In such a case, because the synthesized color can be obtained merely by doping the hole transport layer, there is no need to increase the number of emissive layers.

By using, for the organic compound layer of the element as described above, an organic compound in which an electron attracting substituent is introduced to at least one of the substituents $R_1$~$R_7$ other than the substituents substituted by the substituent represented by the chemical formula (2), an organic EL element can be obtained which has even higher light emitting efficiency or which is capable of being driven at a low voltage. In addition, by introducing an electron donating substituent as a substituent $R_Q$ of Q (aromatic group) in the chemical formula (2), further improvements in the light emitting efficiency can be realized.

BRIEF DESCRIPTION OF DRAWINGS

FIG. 1 is a diagram showing a structure of an organic EL element according to a first embodiment of the present invention.

FIG. 2 is a diagram showing a structure of an organic EL element according to a second embodiment of the present invention.

DESCRIPTION OF REFERENCE NUMERALS

10 SUBSTRATE (TRANSPARENT SUBSTRATE, GLASS SUBSTRATE), 12 FIRST ELECTRODE (ANODE), 14 ORGANIC COMPOUND LAYER, 16 SECOND ELECTRODE (CATHODE), 22 HOLE TRANSPORT LAYER, 24 EMISSIVE LAYER, 26 ELECTRON TRANSPORT LAYER.

BEST MODE FOR CARRYING OUT THE INVENTION

The best mode for carrying out the invention (hereinafter referred to as "the embodiments") will now be described with reference to the drawings.

FIG. 1 schematically shows a structure of an organic EL element according to a first embodiment of the present invention.

The element is constructed by layering a first electrode 12, an organic compound layer 14 which emits light through application of an electric field, and a second electrode 16, in that order, on a transparent substrate 10.

As the transparent substrate 10, a glass substrate, a transparent ceramic substrate, a diamond substrate, or the like can be used. As the first electrode 12, a transparent electrode having a high light transmittance and electrical conductivity is used. For example, a thin film material such as ITO (Indium Tin Oxide), $SnO_2$, $In_2O_3$, or polyaniline can be used.

The organic compound layer 14 is a section which emits light through application of an electric field, and has a structure such as, for example, a single layer structure of an emissive layer, a two-layer structure of a hole transport layer and an emissive layer, or a three-layer structure of a hole transport layer, an emissive layer, and an electron transport layer. The organic compound layer 14 may be formed as a single layer or a multi-layer structure. The thickness of the organic compound layer 14 is in the range of several tens of nanometers to several hundreds of nanometers.

In the first embodiment, a quinoline derivative compound according to the present invention and having a structure which will be described below is used as the material having light emitting function in the organic compound layer 14. The quinoline derivative is capable of forming an emissive layer of the organic EL element as a single entity. It is also possible to form the emissive layer using a known light emitting compound as a host material such as, for example, distyrylarylene derivative (DPVBi) represented by the following chemical formula (4), $Alq_3$, and a derivative of $Alq_3$, and doping, into the host material, for example, on the order of a few percent of a quinoline derivative compound according to the present invention and which will be described below.

(4)

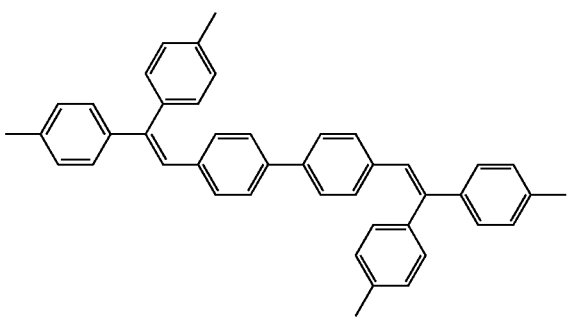

As the hole transport layer and the electron transport layer etc., any known molecules having hole transport functionality and any known molecules having electron transport functionality can be used. Molecules having hole transport functionality include, for example, copper-phthalocyanine and tetramer of triphenylamine (TPTE). Molecules having electron transport functionality include, for example, Alq3 or the like which also has a light emitting function as described above.

As the second electrode 16 to be formed over the organic compound layer 14, a metal electrode such as, for example, Mg, Ag, a Mg—Ag alloy, an Al—Li alloy, and LiF/Al can be used.

In an organic EL element having such a structure, the first electrode 12 is used as an anode and the second electrode 16 is used as a cathode. Holes and electrons are injected from these electrodes into the organic compound layer 14. In the organic compound layer 14, the injected holes and electrons recombine, the light emitting material is excited, and fluorescence of the quinoline derivative according to the present invention in the yellow~red range can be obtained.

An organic EL element according to a second embodiment of the present invention will now be described with reference to FIG. 2. An organic compound layer 14 has a structure wherein at least a hole transport layer 22 and an emissive layer 24 are layered on a first electrode 12 in that order. In addition, in the example shown in FIG. 2, an electron transport layer 26 is formed between the emissive layer 24 and a second electrode 16.

In the second embodiment, the emissive quinoline derivative compound according to the present invention as will be described below is included in the hole transport layer 22, and light emission of a synthesized color can be realized through combination of the hole transport layer 22 and the emissive layer 24 (or alternatively, an emissive layer which also has the electron transport functionality) in which a light emitting material of a desired color is used. In other words, not only can the quinoline derivative compound according to the present invention produce a fluorescence of yellow~red range when used alone, but can also realize a fluorescence of similar wavelength range (orange~red range) when the quinoline derivative compound is doped to the hole transport layer. Therefore, by using a blue emissive material for the emissive layer and the quinoline derivative compound of the present invention as the doping material of the hole transport layer, it is possible to obtain an organic EL element having white light emitting characteristic through synthesis of the blue light from the blue emissive layer and the orange red light from the hole transport layer. The other structures are identical to those in the first embodiment.

As described above for the first embodiment, the quinoline derivative compound according to the present invention which will be described below can emit light when doped to the emissive layer. In addition, as described above, the quinoline derivative compound can also emit light by being doped into the hole transport layer. Therefore, when, for example, a white light emitting organic EL element is created by combining this compound with another light emitting material, there is no need to provide two emissive layers, that is, it is not necessary to provide an emissive layer for each of materials emitting different color. Because of this, it is possible to realize a white light emitting element using the layered structure as shown in FIG. 2 (hole transport layer/emissive layer/electron transport layer) which is already being proposed and doping the organic compound according to the present invention to the hole transport layer.

Because the quinoline derivative compound according to the present invention as described below can emit light when doped, the amount of material required can be reduced compared to the case where the material is used as the principle constituent of the emissive layer, allowing for minimization of cost of the material for manufacture when a white light emitting element is realized using two light emitting materials.

Furthermore, because it is possible to adjust the color of the emitted light by adjusting the amount of doping to the hole transport layer, the thickness of the hole transport layer, the thickness of the emissive layer, etc., adjustment for obtaining a desired white color light is facilitated.

DESCRIPTION OF THE ORGANIC COMPOUND OF THE INVENTION

An organic compound according to the present invention will now be described. The compound has a structure in which at least two of the substituents $R_1$~$R_7$ in a quinoline ring represented by the following general chemical formula (1) are substituted by a substituent represented by the following chemical formula (2) and having n double bonds (where n is an integer greater than or equal to 1).

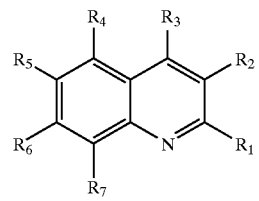

(1)

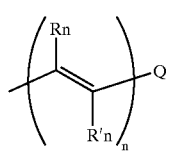

(2)

Because two or more substituent shaving a structure represented by the chemical formula (2) are introduced as the substituents for the quinoline ring represented by the chemical formula (1), the conjugated system of the over all molecule is elongated and the energy differences between the ground state and an excited state are reduced. Thus, for example, by using the compound as a single entity in an emissive layer of an organic EL element or by mixing the compound with another light emitting material (for example, as a doping material to a host material), a light emitting functionality in the range of wavelengths in yellow~red can be obtained which emits light of a wavelength longer than that emitted when known $Alq_3$ (which emits green light) having a quinoline ring is employed.

It is particularly preferable that the terminal group Q in the chemical formula (2) be an aromatic group (aromatic hydrocarbon group or aromatic heterocyclic group). One example of a suitable terminal group Q is a phenyl group represented by the following chemical formula (Q).

Q:

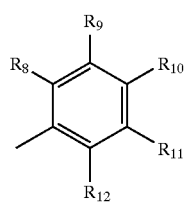

$R_Q$: $R_8$–$R_{12}$

The substituents $R_1$~$R_7$ that are not substituted by a substituent represented by the chemical formula (2) are independent from each other, and hydrogen atom or any arbitrary substituent other than the hydrogen atom can be employed. For example, any of a hydrogen atom, a hydroxy group, a halogen atom, an alkyl group, an alkyl thio group, an aryl group, an aryl thio group, an aryl oxy group, an alkoxy group, an amino group, a cyano group, a nitro group, an ester group, a carboxyl group, a heterocyclic group, and derivatives of these groups can be employed. Each of the substituents can be further substituted by another substituent. Moreover, among the groups other than the substituents substituted by the substituent represented by the chemical formula (2), any one of pairs $R_1$ and $R_2$, $R_2$ and $R_3$, $R_3$ and $R_4$, $R_4$ and $R_5$, $R_5$ and $R_6$, and $R_6$ and $R_7$ may be bonded to form an aromatic ring or an aliphatic ring, and the aromatic ring or the aliphatic ring may be substituted by other substituents. Substituents that can be employed as the substituents of the aromatic ring or the aliphatic ring are similar to the functional groups listed above. Furthermore, in addition to the functional groups formed of carbon and hydrogen such as a benzene ring and naphthalene ring, the bonded aromatic ring or aliphatic ring may also be a ring including a heteroatom. Examples of a heteroatom include nitrogen, oxygen, sulfur, and silicon.

For the substituents $R_n$, and $R'_n$, in the chemical formula (2), any arbitrary functional group may be employed. These substituents $R_n$ and $R'_n$ are independent from each other, and the examples include a hydrogen atom, a hydroxy group, a halogen atom, an alkyl group, an alkyl thio group, an aryl group, an aryl thio group, an aryl oxy group, an alkoxy group, an amino group, a cyano group, a nitro group, an ester group, a carboxyl group, a heterocyclic group, and derivative groups of these groups, for example, a substituent in which a portion of the substituent is substituted by any of the listed substituents. When the number n in the chemical formula (2) is 2 or greater, the substituents $R_n$ and $R'_n$ of the double bond may all be the same, all be different, or some may be the same. As will be exemplified later, by using a structure in which the $R_n$ and $R'_n$ are cyclized, it is possible to block free rotation of the carbon atoms that are doubly bonded in the chemical formula (2). Because of this, it is possible to prevent alteration of the torsional structure of the molecule of the quinoline derivative compound of the present invention, to reduce cutting of the n bond within the molecule, and to facilitate retention of the molecular shape, resulting in the possibility of significant improvements in the thermal durability and stability of light emission in a thin film for which the material is used.

Example compounds having the characteristics described above include the following compounds represented by the chemical formulae (5)~(13) and (14)~(16).

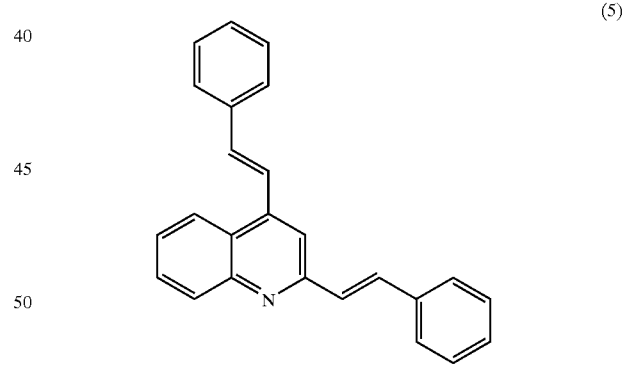

(5)

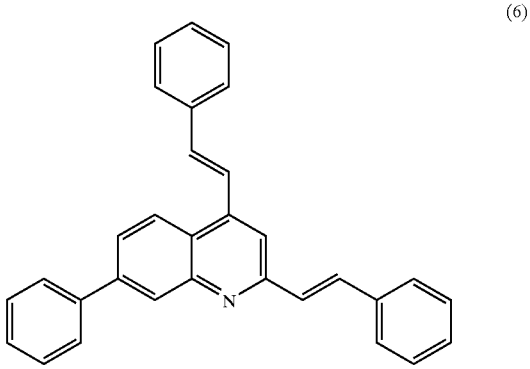

(6)

(7)
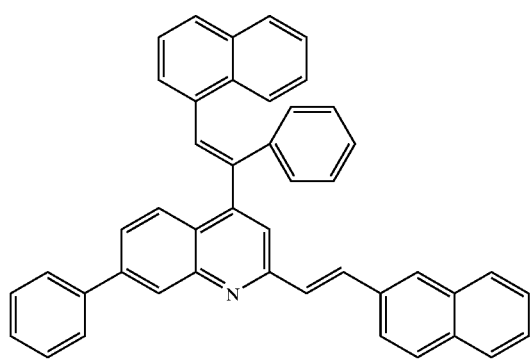
(8)
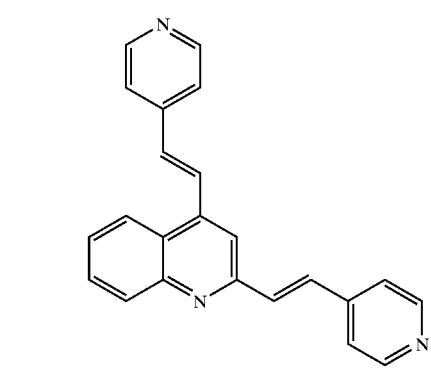
(9)
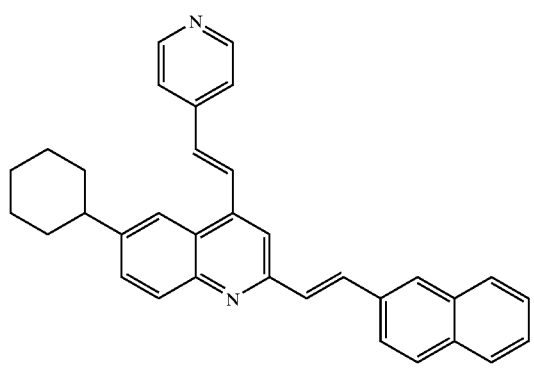
(10)
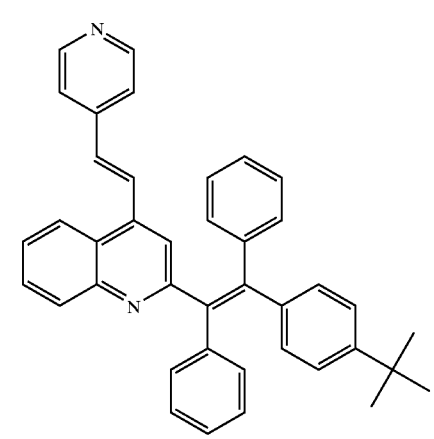
(11)
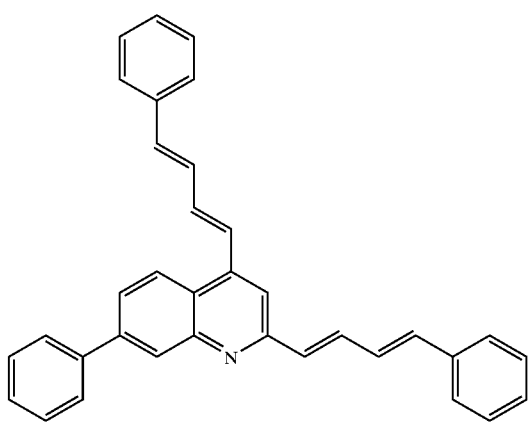
(12)
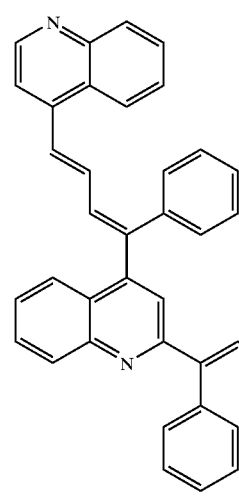
(13)
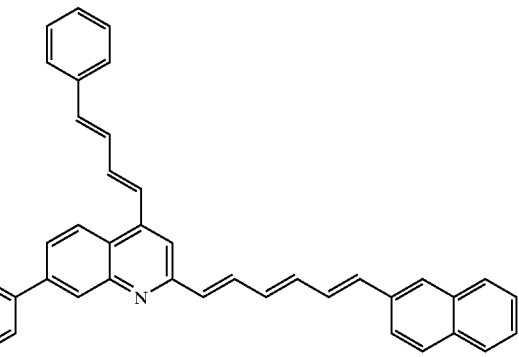
(14)

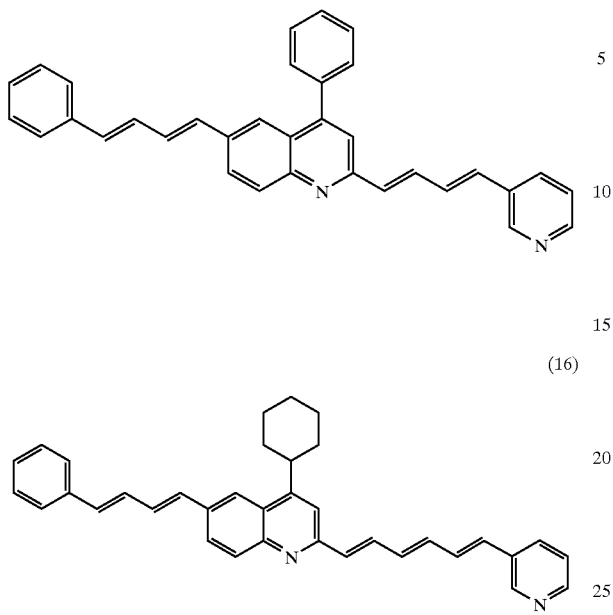

(15)

(16)

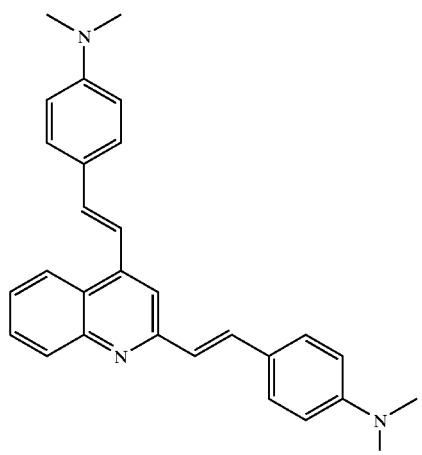

(17)

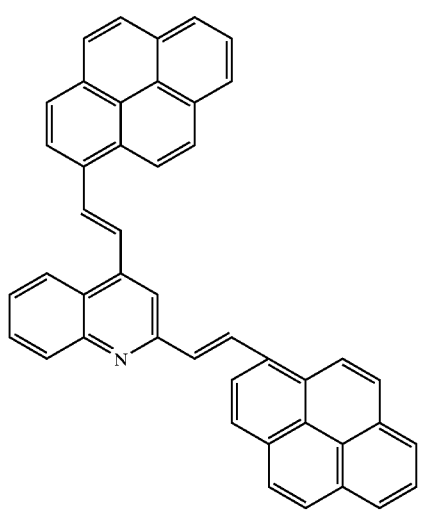

(18)

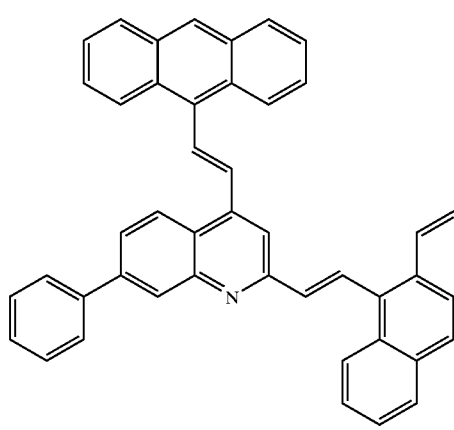

(19)

In the compounds represented by the chemical formulae (5)~(13), substituents represented by the chemical formula (2) are introduced at the $R_1$ and $R_3$ positions in the quinoline ring represented by the chemical formula (1). In the compounds represented by the chemical formulae (14)~(16), substituents represented by the chemical formula (2) are introduced at the $R_1$ and $R_5$ positions in the quinoline ring represented by the chemical formula (1).

(i) Terminal Q in the Chemical Formula (2)

An aromatic group (aromatic hydrocarbon group or aromatic heterocyclic group), such as the phenyl group described above, may be preferably employed as the terminal Q because when an aromatic group is present as the terminal, the reactivity of n double bonds in the chemical formula (2) can be reduced and the stability of the compound can be improved. The substituents $R_Q$ of the terminal Q (substituents $R_8$~$R_{12}$ in the above described phenyl group) are not limited and are independent from each other. For example, a hydrogen atom, a hydroxy group, a halogen atom, an alkyl group, an alkyl thio group, an aryl group, an aryl thio group, an aryl oxy group, an alkoxy group, an amino group, a cyano group, a nitro group, an ester group, a carboxyl group, a heterocyclic group, derivatives of these functional groups (for example, a substitution product in which a portion is substituted by any of the listed functional groups), or the like can be employed. It is also possible for the substituents $R_Q$ to have a structure such that the adjacent substituents $R_Q$ (for example, $R_8$ and $R_9$, $R_9$ and $R_{10}$, $R_{10}$ and $R_{11}$, and $R_{11}$ and $R_{12}$) are bonded to each other to form an aromatic ring or an aliphatic ring. Moreover, the structure may also be such that the aromatic ring or the aliphatic ring is substituted by any of the listed functional groups. Furthermore, these aromatic group and aliphatic group may include a heteroatom within the ring. Example of the heteroatom include, for example, nitrogen, oxygen, sulfur, and silicon.

As the terminal Q, the structures similar to the compounds represented by the following chemical formulae (17)~(24) can be employed.

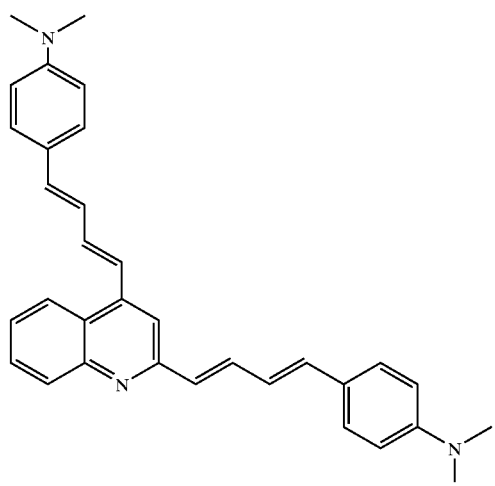
(20)
(21)
(22)

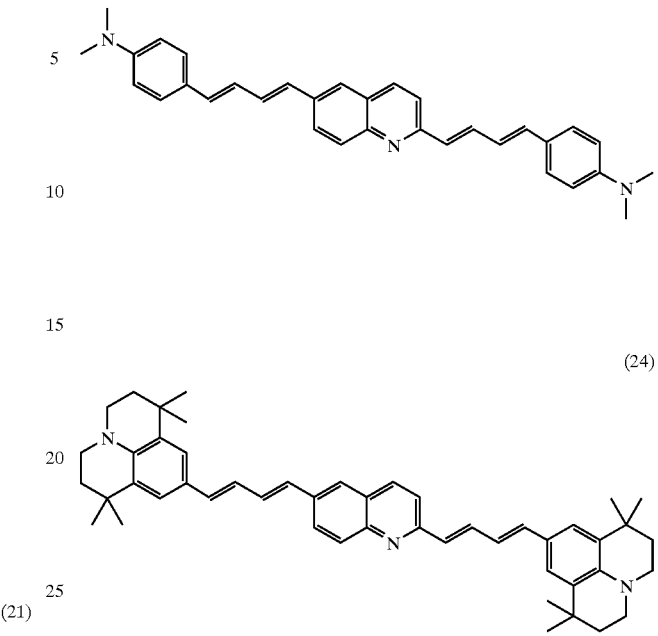
(23)
(24)

In the above compounds, as the terminal Q in the chemical formula (2), a phenyl group (for example, chemical formula (17)), a pyrenyl group (for example, chemical formula (18)), an anthryl group (for example, chemical formula (19)) or the like is employed. In these examples, as the substituents $R_Q$ of the terminal Q, an amino group (for example, chemical formulae (17) and (20)), an isopropyl group or a t-butyl group (for example, chemical formula (22)), a structure in which adjacent groups are bonded to each other to form an aliphatic ring (for example, a julolidyl group in the chemical formula (24)), or the like is employed.

(ii) Substituents Among the Substituents $R_1$~$R_7$ in the Chemical Formula (1) Other than the Substituents Substituted by a Functional Group Represented by the Chemical Formula (2)

As described, at least two of the substituents in the quinoline ring are substituents represented by the chemical formula (2), and the remaining substituents are not limited. However, it is preferable that an electron attracting substituent is introduced to at least one of the remaining substituents among the substituents $R_1$~$R_7$. When an electron attracting substituent is introduced in this manner, the fluorescence quantum yield of the compound is improved, and, when the compound is used as the material for the emissive layer, for example, to form an organic EL element, it is possible to obtain an element having a high emission luminance. Examples of electron attracting substituents include a halogen atom, a cyano group, an ester group, a nitro group, a carbonyl group, and an alkyl group and an aryl group substituted by these listed functional groups.

For example, it is possible to employ functional groups represented by the following chemical formulae (25)~(27) and (28~(30) as an electron attracting substituent for introduction to the quinoline derivative compound according to the present invention.

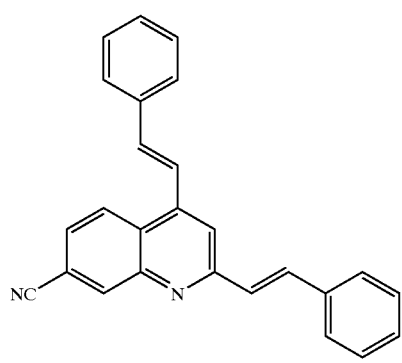

(25)

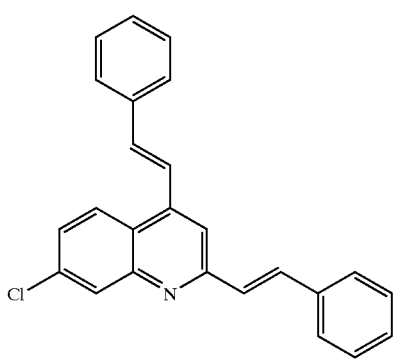

(26)

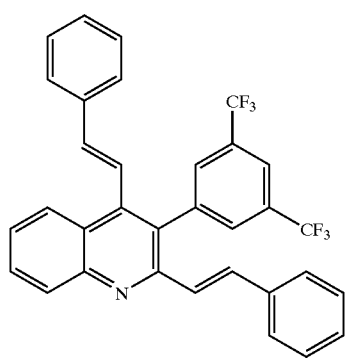

(27)

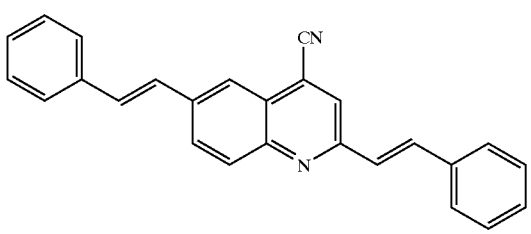

(28)

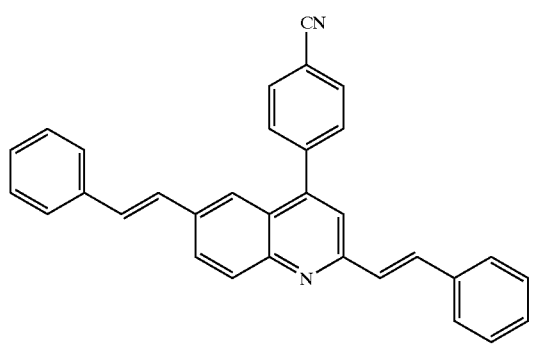

(29)

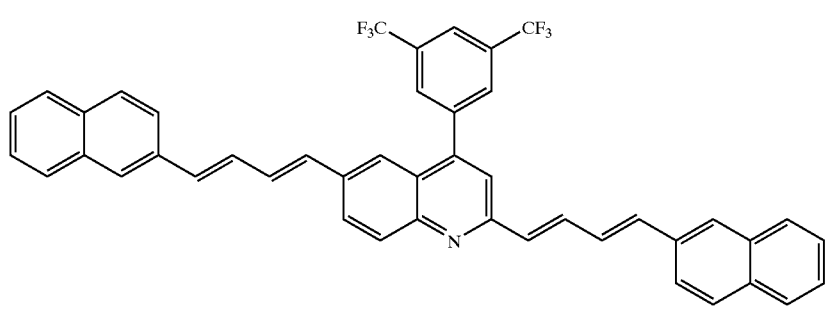

(30)

In the above compounds, for example, in the chemical formulae (25) and (28), cyano groups are employed, in the chemical formula (26), a chlorine atom is employed, and in the chemical formulae (27), (29), and (30), phenyl groups which includes an electron attracting functional group (an alkyl group to which a cyano group, a halogen atom, or the like is introduced) are employed.

(iii) Substituents $R_Q$ of the Terminal Group Q of Chemical Formula (2)

In the present invention, the substituents $R_Q$ are not limited to any particular subsituent. However, by employing an electron donating substituent, it is possible to improve the fluorescence quantum yield of the organic compound and to obtain an organic EL element having a high emission luminance by using such a compound as the light emitting material. Examples of electron donating substituents include an amino group, an alkoxy group, an alkyl thio group, an alkyl group, and an amino group substituted by an alkyl group. Also, by employing a structure in which any of the listed electron donating substituents is introduced to an aromatic ring or an aliphatic ring in cases where adjacent substituents $R_Q$ (for example, in the above chemical formula (Q), $R_8$ and $R_9$, $R_9$ and $R_{10}$, $R_{10}$ and $R_{11}$, and $R_{11}$ and $R_{12}$) are bonded to each other to form an aromatic ring or an aliphatic ring, it is possible to improve the fluorescence quantum yield, similar to the above.

(iv) Interaction Between the Substituents $R_1$~$R_7$ and the Substituents $R_Q$ of the Terminal Group Q of Chemical Formula (2)

By both introducing an electron attracting functional group to at least one of the substituents $R_1$~$R_7$ of the quinoline ring which are not substituted by the functional group represented by the chemical formula (2) as described above in (ii) and introducing an electron donating functional group into at least one of the subsitutents $R_Q$ of the terminal group Q of the chemical formula (2) as described above in (iii), it is possible to further improve the fluorescence quantum yield in comparison to a compound that satisfies only one of the conditions (ii) and (iii). Therefore, by using a compound which satisfies this condition (iv), it is possible to obtain a brighter organic EL element.

Example compounds satisfying the above conditions include the compounds represented by the following chemical formulae (31)~(34) and (35)~(39).

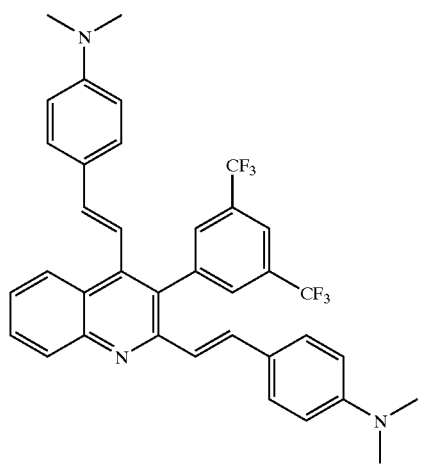

(31)

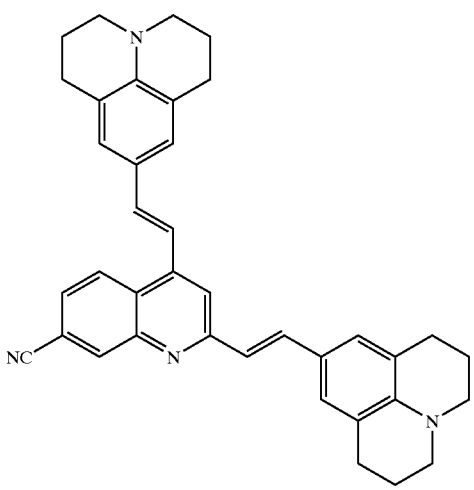

(32)

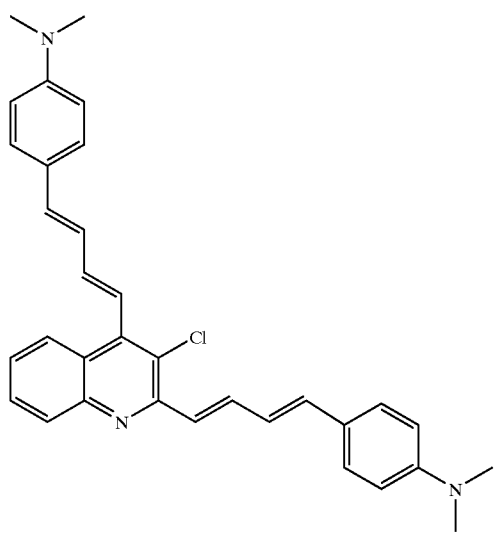

(32)

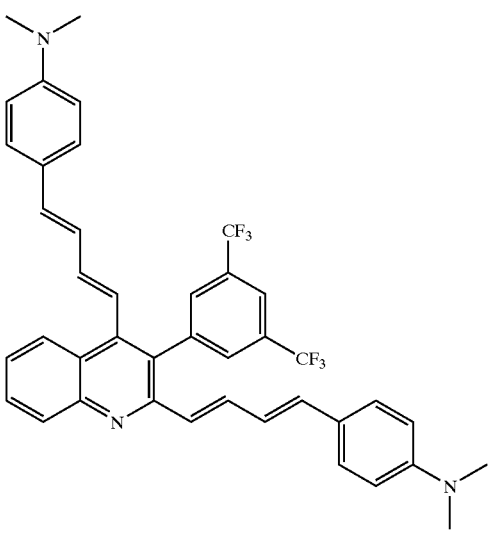

(34)

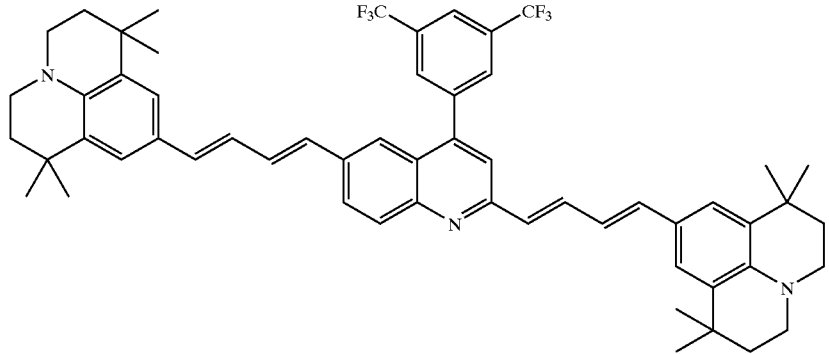

(35)

-continued
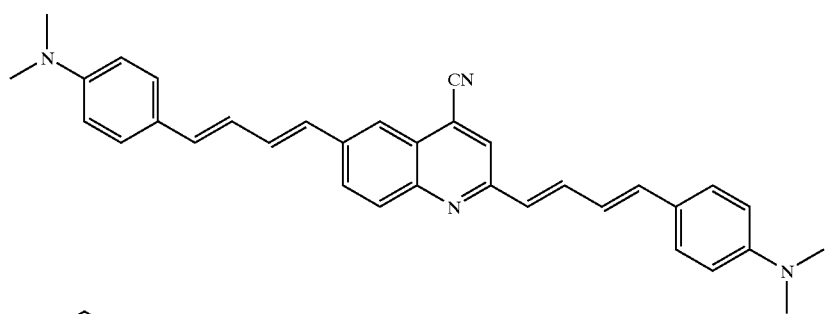
(36)
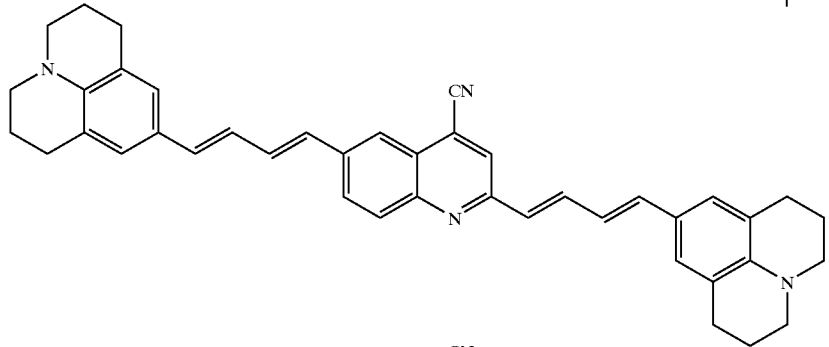
(37)
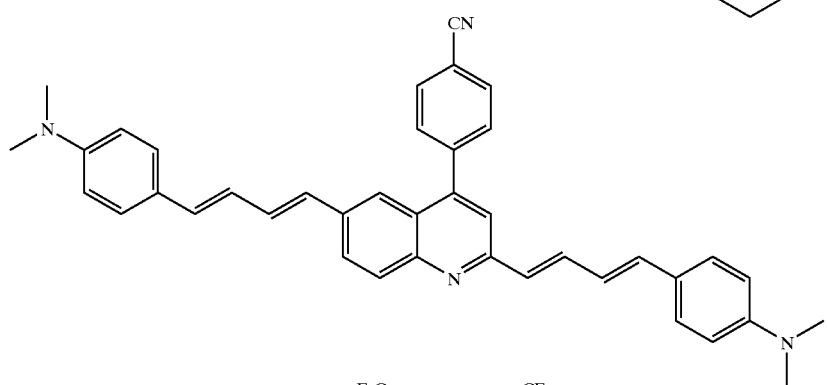
(38)
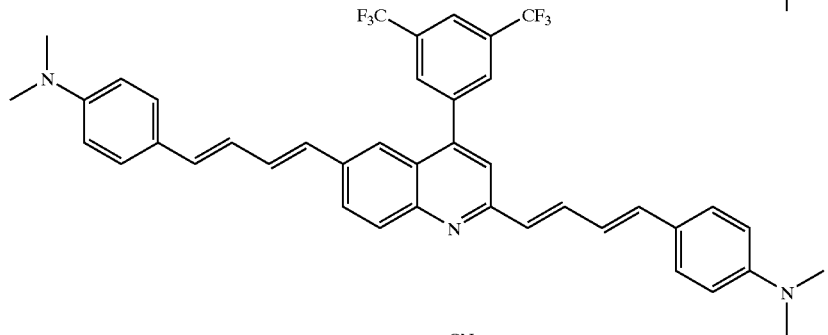
(39)
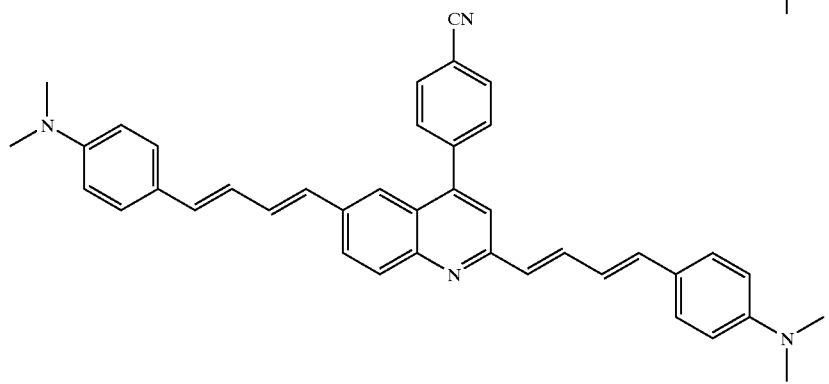
(38)

-continued

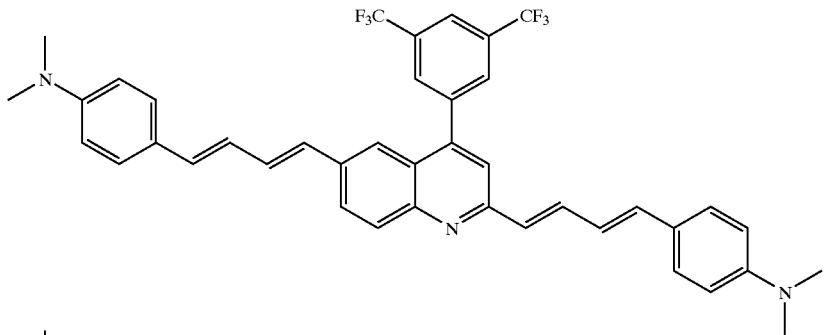
(39)

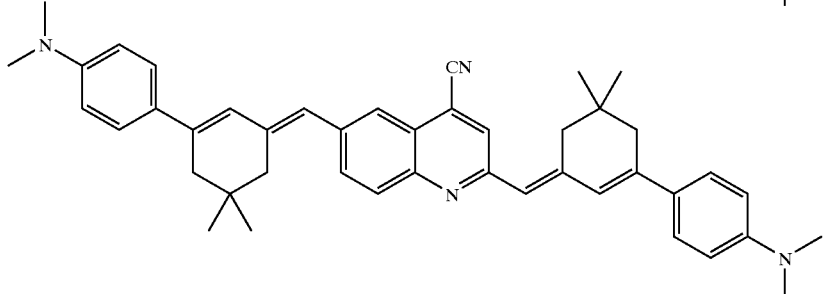
(40)

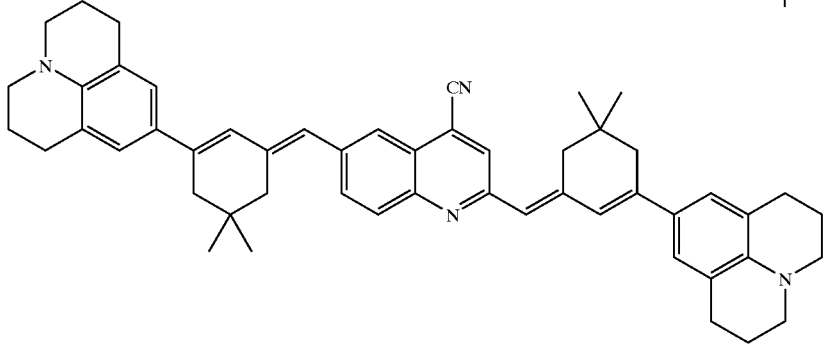
(41)

Moreover, it is possible to obtain a red-based light emitting material having a superior stability and thermal endurance by employing a CN group having a superior electron attracting capability in the substituent $R_3$ of the quinoline ring represented by the chemical formula (1) and a p-aminophenyl group having a superior electron donating capability as the terminal group Q of the chemical formula (2), as shown in the above chemical formula (36).

(v) Number n of the Vinyl Group in the Chemical Formula (2)

As stated above, the number n (a number greater than or equal to 1) in the chemical formula (2) is not limited. However, it is preferable that n be 5 or less. If the number n becomes equal to or greater than 6, the stability of the compound is degraded and a highly durable element cannot be obtained when the compound is used for an organic EL element. It is still more preferable that the number n be an integer in the range of 1~3. When the number n is within the range of 1~3, the compound is highly stable, and the endurance of the organic EL element can be improved when the compound is used for the organic EL element.

Also, when the number n is within the range of 1~3, the light emitting efficiency is improved, and, thus, a compound which is superior as a material having a light emitting functionality can be obtained. In particular, when the number n equals 2, the light emitting efficiency of the compound is further improved. For example, when an emissive layer of an organic EL element is formed by doping a compound in which the number n is within the range of 1~3, and, in an optimal case, equals 2, to a host material, the compound not only is highly stable, but also can efficiently receive energy from the host material and emit light, thereby allowing for a highly efficient light emission.

(vi) Endurance

As described above in (v), in a compound in which the n is 5 or less, in particular, in a range of 1~3, because of reasons such as an increase in the molecular weight, molecules of such a compound are relatively immovable in a film when a thin film is made from the compound, and thus, the stability of the film, that is, the endurance of the film, can be improved.

Moreover, when a bulky functional group is employed as the terminal group Q in the chemical formula (2) to be introduced to the quinoline ring and as the functional group (for example, an electron attracting group) to be introduced to the remaining substituents of the quinoline ring, the crystallinity of the molecule is reduced because of steric hindrance or the like. By forming a film using such a compound including a bulky functional group, the cohesion of the compound within the film occurs less frequently, resulting in improvements in the thermal durability (endurance) of the film.

Furthermore, superior characteristics can be obtained in quinoline derivative compounds having structures represented by the following chemical formulae (40)~(45).

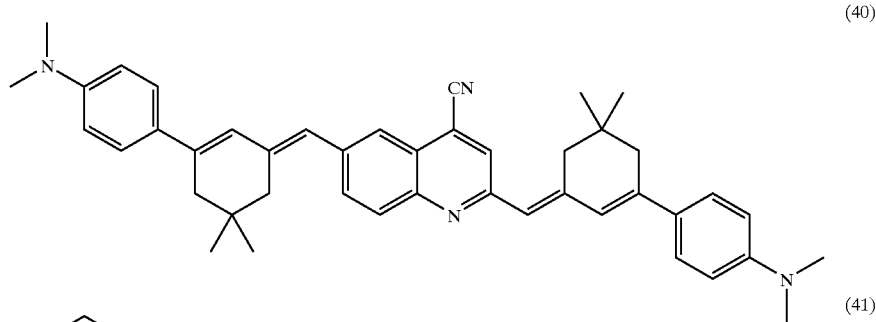
(40)
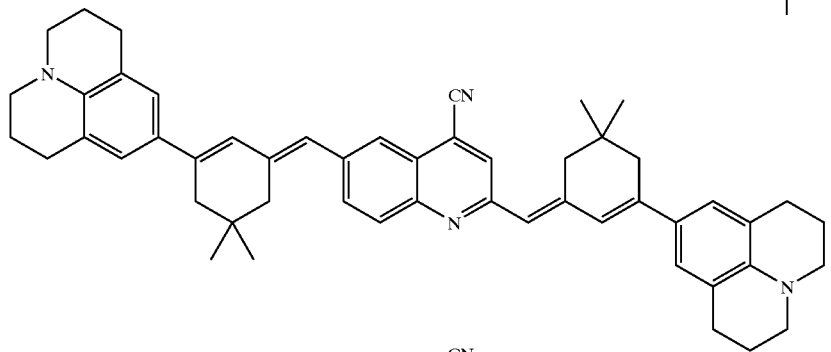
(41)
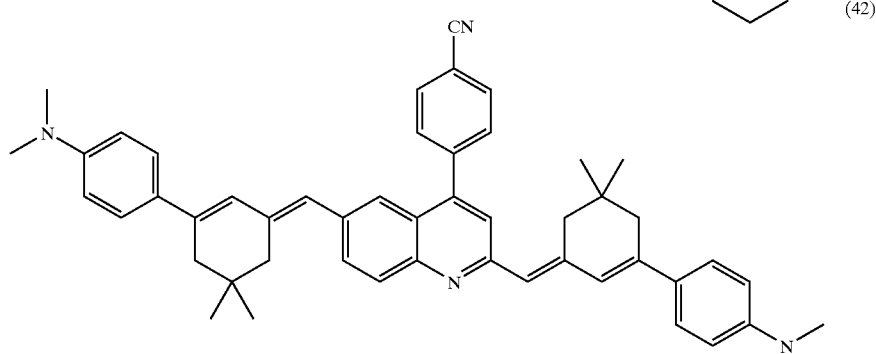
(42)
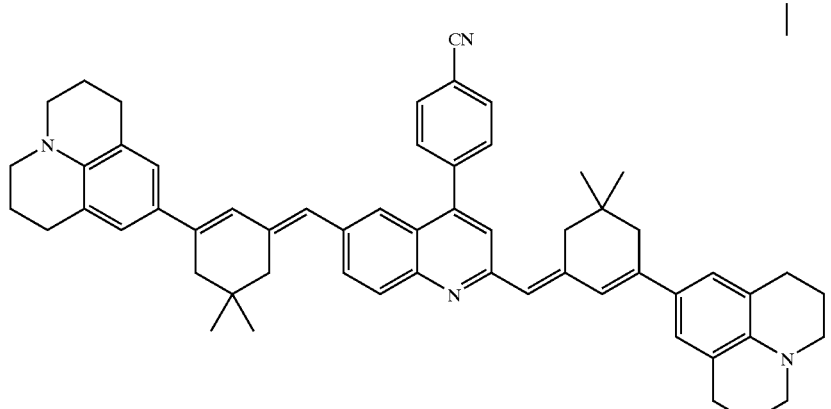
(43)
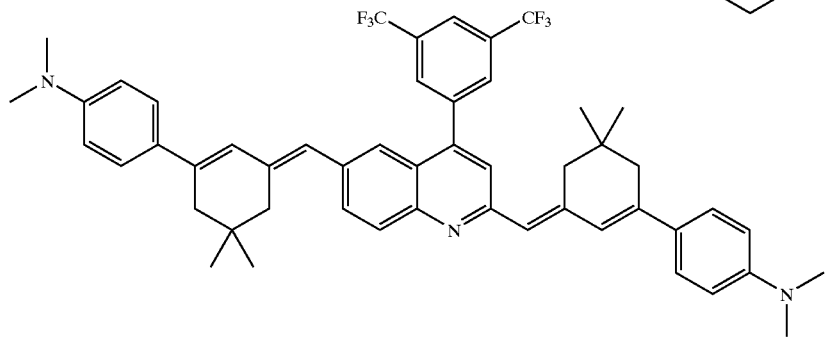
(44)

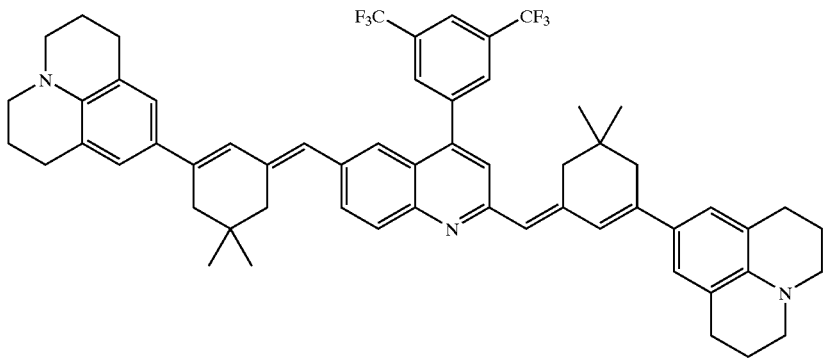

(45)

In these compounds, the number n in the chemical formula (2) is set at 2, a substituent having a superior electron attracting capability such as, for example, a cyano group, a p-cyano phenyl group, and 3,5-bis(trifluoromethyl)phenyl group is introduced to the substituent $R_3$, substituents having a superior electron donating capability such as, for example, ap-aminophenyl group and a julolidyl group is introduced as the substituent Q to the substituents $R_1$ and $R_5$, and $R_n$ and $R'_n$ in the chemical formula (2) are cyclized. In such a structure, the molecular structure is stable, and, when a thin film is made, the film has a superior endurance. Moreover, a longer chain of n bonds is present within the molecule and superior light emitting characteristic can be realized. Furthermore, these molecules demonstrate a light emitting characteristic even when doped to the hole transport layer, and it is therefore possible to easily obtain a color synthesized with the light from the emissive layer. In particular, by combining a blue emissive layer and a hole transport layer which is doped by these quinoline derivative compounds, it is possible to easily realize a superior white light emitting organic EL element.

EXAMPLES

Specific examples of the realization of the present invention and comparative examples will now be described.

Example 1-1

Synthesis of a Compound Represented by the Chemical Formula (20)

In example 1-1, a compound represented by the above chemical formula (20) was synthesized as an example quinoline derivative compound through the following processes.

2,4-dimethylquinoline (2.0 g), N-bromosuccinimide (4.5 g), benzoyl peroxide (500 mg), and $CCl_4$ (50 ml) were mixed and heated and refluxed for 2 hours in a nitrogen atmosphere. The reaction solution was cooled to room temperature and succinimide produced through the reaction was removed by filtering. The solvent was removed under reduced pressure and the residue was purified through column chromatography (silica gel, hexane/ethyl acetate=4/1) to obtain 2,4-bis(bromomethyl)quinoline (0.93 g).

A toluene solution (5 ml) of the 2,4-bis(bromomethyl) quinoline thus obtained (0.93 g) and triethyl phosphite (3.3 ml) were heated in a nitrogen atmosphere for 3 hours at a temperature of 140° C. The reaction solution was cooled to room temperature and excessive triethyl phosphite and toluene were removed, to obtain coarse refinement of Wittig reagent of 2,4-bis(bromomethyl)quinoline.

A DMF (N,N-dimethylformamide) (2 ml) solution of the coarse refinement of Wittig reagent of 2,4-bis(bromomethyl) quinoline obtained as above and N,N-dimethylaminocinnamaldehyde) (0.35 g) were dropped to a mixture of sodium t-butoxide (0.38 g) and DMF (2 ml) in a nitrogen atmosphere and at room temperature, and the reaction solution was stirred for 2 hours at room temperature. Water was added to the reaction solution and organic layer was extracted using ethyl acetate. The organic layer was dried by $Na_2SO_4$ and the $Na_2SO_4$ was then removed by filtering. The solvent was removed under reduced pressure and the residue was purified through column chromatography (silica gel, hexane/ethyl acetate=3/2) to obtain a compound represented by the chemical formula (20) (0.3 g).

Example 1-2

Synthesis of a Compound Represented by the Chemical Formula (34)

In this example 1-2, a compound represented by the above chemical formula (34) was synthesized as an example quinoline derivative. The compound represented by the chemical formula (34) was obtained through a method similar to the example 1-1 for synthesis of the compound represented by the chemical formula (20) except that 2,4-dimethyl-3-[3,5-bis(trifluoromethyl)phenyl]quinoline was used in place of 2,4-dimethylquinoline.

2,4-dimethyl-3-[3,5-bis(trifluoromethyl)phenyl]quinoline was synthesized through the following processes. First, 2,3-dimethylindole (1.0 g), triethylbenzylammonium chloride (0.17 g), $CHCl_3$ (10 ml), and an aqueous solution of NaOH (33%, 5 ml) were mixed at a temperature of 0° C. and were stirred for 6 hours at 0° C. and then for 24 hours at room temperature. The organic layer was extracted using $CHCl_3$ and the solvent was removed under reduced pressure. The residue was purified through column chromatography (silica gel, hexane/ethyl acetate=3/1) to obtain 2,4-dimethyl-3-chloroquinoline (0.65 g).

To a THF solution of the obtained 2,4-dimethyl-3-chloroquinoline (0.65 g) and $Ni(dpp)Cl_2$ (dpp: 1,3-bis(diphenylphosphino)propane) (0.1 g), 3,5-bis(trifluoromethyl)phenylmagnesium bromide prepared from Mg and 3,5-bis(trifluoromethyl)bromobenzene was dropped and the reaction solution was allowed to react for 24 hours at room temperature. Water was added to the reaction solution and the organic layer was extracted using $CHCl_3$. The solvent was removed under reduced pressure and the residue was purified through column chromatography to obtain 2,4-dimethyl-3-[3,5-bis(trifluoromethyl)phenyl] quinoline.

Example 1-3

Synthesis of a Compound Represented by the Chemical Formula (35)

In the example 1-3, a compound represented by the chemical formula (35) was synthesized. The compound represented by the chemical formula (35) was obtained through a synthesis similar to example 1-1 for synthesizing the compound represented by the chemical formula (20), except that 2,6-dimethyl-4-[3,5-bis(trifluoromethyl)phenyl] quinoilne was used in place of 2,4-dimethylquinoline and a compound represented by the following chemical formula (46) was used in place of the N,N-dimethylaminocinnamaldehyde.

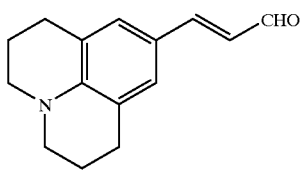

(46)

2,6-dimethyl-4-[3,5-bis(trifluoromethyl)phenyl]quinoline was synthesized through the following processes.

First, 3,5-bis(trifluoromethyl)phenylmagnesium bromide prepared from Mg and 3,5-bis(trifluoromethyl) bromobenzene was dropped into a THF solution of 4-chloro-2,6-dimethylquinoline (1 g) andNi(dpp)Cl$_2$ (dpp: 1,3-bis (diphenylphosphino)propane) (0.1 g). Reactions were allowed to take place for 24 hours at room temperature. Water was added to the reaction solution and the organic layer was extracted using CHCl$_3$. The solvent was removed under reduced pressure and the residue was purified through column chromatography to obtain 2,6-dimethyl-4-[3,5-bis (trifluoromethyl)phenyl]quinoline (0.5 g).

Example 1-4

Synthesis of a Compound Represented by the Chemical Formula (36)

In example 1-4, a compound represented by the chemical formula (36) was synthesized through the following processes as an example quinoline derivative.

First, 4-bromo-2,6-dimethylquinoline (5.0 g) and CuCN (4.82 g) were added to DMF (70 ml) and were allowed to react for 6 hours at a temperature of 140° C. Ice was poured to the reaction solution and the produced precipitate was removed through filtering. The filtrate was extracted using ethyl acetate, the solvent was removed under reduced pressure, and the residue was purified through column chromatography (silica gel, hexane/ethyl acetate=4/1) to obtain 4-cyano-2,6-dimethylquinoline (2.14 g) represented by the following chemical formula (47).

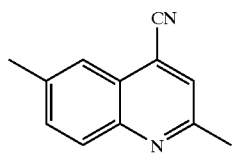

(47)

The 4-cyano-2,6-dimethylquinoline (2.0 g), n-bromosuccinimide (3.91 g), benzoyl peroxide (0.430 g), and CCl$_4$ (50 ml) were mixed and heated and refluxed for 1.5 hours in a nitrogen atmosphere. The reaction solution was cooled to room temperature and succinimide produced through the reaction process was removed by filtering. The solvent was removed under reduced pressure and the residue was purified through column chromatography (silica gel, hexane/ethyl acetate=4/1) to obtain 4-cyano-2,6-bis(bromomethyl) quinoline (0.18 g).

A toluene (1 ml) solution of the 4-cyano-2,6-bis (bromomethyl) quinoline (0.80 g) and triethyl phosphite (1 ml) was heated for 2.5 hours in a nitrogen atmosphere at a temperature of 140° C. The reaction solution was cooled to room temperature and excessive triethyl phosphite and toluene were removed to obtain a coarse product of Wittig reagent of 4-cyano-2,6-bis(bromomethyl)quinoline.

A DMF (N,N-dimethylformamide) (2 ml) solution of the coarse product of the Wittig reagent of 4-cyano-2,6-bis (bromomethyl)quinoline and N,N-dimethylaminocinnamaldehyde (0.124 g) was dropped into a mixture of sodium t-butoxide (0.091 g) and DMF (2 ml) in a nitrogen atmosphere at room temperature and stirring was performed for 3 days at room temperature. Water was added to the reaction solution and the produced precipitate was filtered. The precipitate was washed by a CCl$_4$ water and vacuum dried to obtain a compound represented by the chemical formula (36) (0.10 g).

Example 1-5

Synthesis of a Compound Represented by the Chemical Formula (37)

In example 1-5, a compound represented by the chemical formula (37) was synthesized through the following processes as an example quinoline derivative. A DMF (2 ml) solution of the coarse product of Wittig reagent of 4-cyano-2,6-bis(bromomethyl)quinoline which was synthesized through a process similar to the process for the above compound represented by the chemical formula (36) and aldehyde (0.160 g) represented by the chemical formula (47) was dropped to a mixture of sodium t-butoxide (0.091 g) and DMF (2 ml) in a nitrogen atmosphere and at room temperature, and stirring was performed for 5 days at room temperature. Water was added to the reaction solution and the produced precipitate was filtered. The precipitate was washed by CCl$_4$ water and vacuum dried to obtain a compound represented by the chemical formula (37) (0.108 g).

Example 1-6

Synthesis of a Compound Represented by the Chemical Formula (38)

In example 1-6, a compound represented by the chemical formula (38) was synthesized through the following processes as an example quinoline derivative. First, a solution in which 4-bromo-2,6-dimethylquinoline (1.05 g) identical to that in the example 1-4 and Pd(Ph$_3$P)$_4$ (0.31 g) were added to toluene (8.5 ml), a solution in which Na$_2$CO$_3$ (1.81 g) was added to water (8.5 ml), and a solution in which 4-cyanophenylboric acid (0.726 g) was added to methanol (2.8 ml) were mixed and allowed to react for 22 hours in a nitrogen atmosphere at a temperature of 80° C. The reaction solution was poured into water and extracted using chloroform. The chloroform layer was dried using Na$_2$SO$_4$ and the Na$_2$SO$_4$ was removed by filtering. The solvent was removed under reduced pressure and the residue was purified through column chromatography (silica gel, hexane/ethyl acetate=2/1) to obtain 4-(4-cyanophenyl)-2,6-dimethylquinoline (1.013 g) represented by the following chemical formula (48).

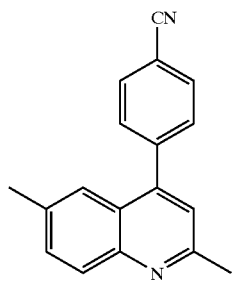

(48)

The 4-(4-cyanophenyl)-2,6-dimethylquinoline (1.1 g), N-bromosuccinimide (1.516 g), benzoyl peroxide (165 mg), and $CCl_4$ (20 ml) were mixed and heated and refluxed for 1.5 hours in a nitrogen atmosphere. The reaction solution was cooled to room temperature and the succinimide produced by the reaction was removed by filtering. The solvent was removed under reduced pressure and the residue was purified through column chromatography (silica gel, hexane/ethyl acetate=4/1) to obtain 4-(4-cyanophenyl)-2,6-bis(bromomethyl)quinoline (0.098 g).

A toluene (1 ml) solution of 4-(4-cyanophenyl)-2,6-bis(bromomethyl)quinoline (0.095 g) and triethyl phosphite (1 ml) was heated for 2.5 hours at a temperature of 140° C. The reaction solution was cooled to room temperature and excessive triethyl phosphite and toluene were removed to obtain a coarse product of Wittig reagent of 4-(4-cyanophenyl)-2,6-bis(bromomethyl)quinoline.

A DMF (2 ml) solution of the coarse product of Wittig reagent of 4-(4-cyanophenyl)-2, bis(bromomethyl)quinoline and N,N-dimethylaminocinnamaldehyde (0.120 g) was dropped to a mixture of sodium t-butoxide (0.090 g) and DMF (2 ml) in a nitrogen atmosphere at room temperature and stirring was performed for 3 days at room temperature. Water was added to the reaction solution and the produced precipitate was filtered. The precipitate was washed using $CCl_4$ water and vacuum dried to obtain a compound represented by the chemical formula (38) (0.125 g).

Example 1-7

Synthesis of a Compound Represented by the Chemical Formula (39)

In example 1-7, a compound represented by the chemical formula (39) was synthesized through the following processes as an example quinoline derivative.

Magnesium (1.60 g) was added to THF (60 ml) in a nitrogen atmosphere and 3,5-bis (trifluoromethyl) phenylbromide (17.58 g) was dropped. The resulting mixture was stirred for 30 minutes at room temperature and a THF solution of 3,5-bis (trifluoromethyl)phenylmagnesiumbromide was prepared. In a nitrogen atmosphere, 4-chloro-2,6-dimethylquinoline (2.88 g) and $Ni(dpp)Cl_2$ (500 mg) were added to THF (30 ml) and dispersed. The THF solution of 3,5-bis(trifluoromethyl)phenylmagnesiumbromide prepared as above was dropped to the suspension and the resulting solution was stirred for 4 days at room temperature. Water was poured into the reaction solution, impurities were filtered, and extraction was performed using AcOEt (ethyl acetate). A drying process was applied using $Na_2SO_4$ and the solvent was removed under a reduced pressure. The residue was purified through a silica gel column (hexane/ethyl acetate=3/2) to obtain 4-(3,5-bis(trifluoromethyl)phenyl)-2,6-dimethylquinoline (4.40 g) represented by the following chemical formula (49).

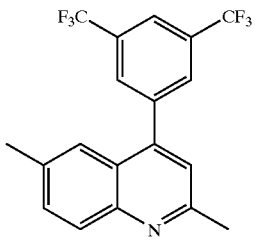

(49)

4-(3,5-bis(trifluoromethyl)phenyl)-2,6-dimethylquinoline as represented by the chemical formula (49), N-bromosuccinimide (3.85 g), benzoyl peroxide (400 mg), and $CCl_4$ (50 ml) were heated and refluxed in a nitrogen atmosphere for 3 hours. The reaction solution was cooled to room temperature and the succinimide produced through the reaction was removed by filtering. The solvent was removed under reduced pressure and the residue was purified through column chromatography (silica gel, hexane/ethyl acetate=4/1) to obtain 4-(3,5-bis(trifluoromethyl)phenyl)-2,6-bis(bromomethyl)quinoline (0.353 g).

A toluene (2 ml) solution of 4-(3,5-bis(trifluoromethyl)phenyl)-2,6-bis(bromomethyl)quinoline (0.100 g) and triethyl phosphite (2 ml) was heated for 2.5 hours in a nitrogen atmosphere at a temperature of 140° C. The reaction solution was cooled to room temperature and excessive triethyl phosphite and toluene were removed to obtain a coarse product of Wittig reagent of 4-(3,5-bis(trifluoromethyl)phenyl)-2,6-bis(bromomethyl)quinoline.

A DMF (2 ml) solution of the coarse product of Wittig reagent of 4-(3,5-bis(trifluoromethyl)phenyl)-2,6-bis(bromomethyl)quinoline and N,N-dimethylaminocinnamaldehyde (0.067 g) was dropped to a mixture of sodium t-butoxide (0.073 g) and DMF (2 ml) in a nitrogen atmosphere at room temperature, and the resulting solution was stirred for 1 day at room temperature. Water was added to the reaction solution and the produced precipitate was filtered. The precipitate was washed using $CCl_4$ water and vacuum dried to obtain the compound represented by the chemical formula (39) (0.058 g).

Example 2-1

Using the compound represented by the chemical formula (20) and created in the example 1-1 as a doping material, an organic electroluminescence element was created through the following process. The structure of the produced element is identical to that shown in FIG. 1. On a glass substrate 10, which is a transparent substrate, an ITO electrode was formed as a first electrode 12 and a hole transport layer, an emissive layer, an electron transport layer were formed as the organic compound layer 14 in that order over the ITO. The hole transport layer was formed by vacuum evaporating TPTE to a thickness of 600 Å. On top of the hole transport layer, a layer in which the compound of the example 1-1 represented by the chemical formula (20) was doped to 0.8 weight % into an $Alq_3$ (chemical formula (3)) which is the host material was evaporated to a thickness of 400 Å to form the emissive layer. Then, $Alq_3$ was evaporated to a thickness of 200 Å to form the electron transport layer. Finally, a LiF/Al electrode were formed as the second electrode 16 by sequentially evaporating LiF and Al, to complete an organic EL element.

The organic EL element thus obtained was driven at room temperature in a nitrogen atmosphere. When the organic EL element was driven with a current density of 11 mA/cm$^2$, light emission with a luminance of 300 cd/m$^2$ was achieved. The emitted light was orange. The luminance half-life when the element was driven with a current density of 110 mA/cm$^2$ was approximately 40 hours.

Example 2-2

An element was created under conditions similar to the example 2-1 except that the compound represented by the chemical formula (34) and created in the example 1-2 was used as the doping material instead of the compound represented by the chemical formula (20) and used in the example 2-1. The obtained organic EL element was driven at room temperature in a nitrogen atmosphere. With a current density of 11 mA/cm$^2$, light emission with a luminance of 350 cd/m$^2$ was achieved. The emitted light was red. The luminance half-life when the element was driven with a current density of 110 mA/cm$^2$ was approximately 40 hours.

Example 2-3

An element was created under conditions similar to the example 2-1 except that the compound represented by the chemical formula (36) and created in the example 1-3 was used as the doping material instead of the compound represented by the chemical formula (20) and used in the example 2-1. The obtained organic EL element was driven at room temperature in a nitrogen atmosphere. With a current density of 11 mA/cm$^2$, light emission luminance of 450 cd/m$^2$ was achieved. The emitted light was red. The luminance half-life of the element when the element was driven with a current density of 110 mA/cm$^2$ was approximately 50 hours.

Comparative Example 1

In a structure similar to that shown in FIG. 1, an ITO electrode was formed as the first electrode 12 on a glass substrate 10 and an organic compound layer 14 (comprising a hole transport layer and an emissive layer which also functions as the electron transport layer) was formed on the ITO. The hole transport layer was formed by vacuum evaporating TPTE to a thickness of 600 Å. On top of the hole transport layer, an emissive layer which also functions as the electron transport layer was formed by evaporating Alq$_3$ represented by the chemical formula (3) to a thickness of 600 Å. Finally, LiF/Al electrode was evaporated as the second electrode 16 to complete an organic EL element. This element was driven at room temperature in a nitrogen atmosphere. When the element was driven with a current density of 11 mA/cm$^2$, a light emission luminance of 250 cd/m$^2$ was achieved. The emitted light was green. The luminance half-life of the element when the element was driven with a current density of 110 mA/cm$^2$ was approximately 50 hours.

Comparative Example 2

An organic EL element was created under the conditions similar to the example 2-1 except that a known porphyrin derivative represented by the chemical formula (50),

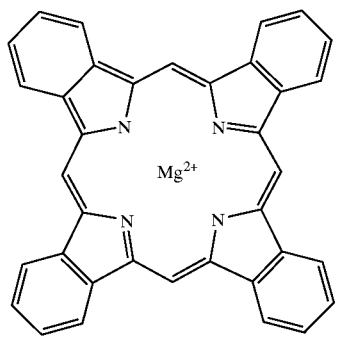

(50)

was used as the doping material instead of the compound represented by the chemical formula (20). The element was driven at room temperature in a nitrogen atmosphere. When the element was driven with a current density of 11 mA/cm$^2$, a light emission luminance of 100 cd/m$^2$ was achieved. The emitted light was red. The luminance half-life of the element when the element was driven with a current density of 110 mA/cm$^2$ was only approximately 10 hours.

Upon comparison of the examples 2-1~2-3 and the comparative examples 1 and 2, it can be seen that by using the quinoline derivative according to the present invention as the doping material for the emissive layer, light in the yellow~red range having a wavelength longer than green light can be produced. It can also be seen that significantly higher light emission luminance can be achieved with the elements of the examples 2-1~2-3, compared to the comparative examples 1 and 2. Furthermore, the luminance half-lives in the examples are similar to that in the comparative example 1 (Alq$_3$) which currently is considered to have a high stability.

Example 3-1

An organic electroluminescence element was created through the following process using as the doping material the compound represented by the chemical formula (36) created in the example 1-4. The structure of the element was identical to that shown in FIG. 2. On a glass substrate 10 as the transparent substrate, an ITO electrode was formed as a first electrode 12 and a hole transport layer 22, an emissive layer 24, and an electron transport layer 26 were formed on the ITO in that order as the organic compound layer 14. The hole transport layer 22 was formed by vacuum evaporating TPTE to a thickness of 500 Å and evaporating a layer in which the compound of the example 1-4 and represented by the chemical formula (36) were doped in 1.0 weight % to TPTE as the host material to a thickness of 100 Å, to form a two-layer hole transport layer 22 of a TPTE single layer and a doped layer. On top of the hole transport layer, DPVBi was evaporated to a thickness of 200 Å to form an emissive layer 24. Then, Alq$_3$ was evaporated to a thickness of 400 Å to form an electron transport layer 26. Finally, LiF and Al were sequentially evaporated to form a LiF/Al electrode as the second electrode 16 to complete an organic EL element.

The organic EL element thus obtained was driven at room temperature in a nitrogen atmosphere. When the element was driven with a current density of 11 mA/cm$^2$, a light emission luminance of 800 cd/m$^2$ was achieved. The emitted light was white. The luminance half-life when the element was driven with a current density of 110 mA/cm$^2$ was approximately 50 hours.

Example 3-2

An organic EL element was created under the conditions similar to those in the example 3-1 except that the compound created in the example 1-5 and represented by the chemical formula (38) was used as the doping material instead of the compound represented by the chemical formula (36) which was doped to the hole transport layer in the example 3-1. The organic EL element thus obtained was driven at room temperature in a nitrogen atmosphere. When the element was driven with a current density of 11 mA/cm$^2$, a light emission luminance of 800 cd/m$^2$ was achieved. The emitted light was white. The luminance half-life when the element was driven with a current density of 110 mA/cm$^2$ was approximately 50 hours.

Example 3-3

An organic EL element was created under the conditions similar to those in the example 3-1 except that the compound created in the example 1-7 and represented by the chemical formula (39) was used as the doping material instead of the compound represented by the chemical formula (36) which was doped to the hole transport layer in the example 3-1. The organic EL element thus obtained was driven at room temperature in a nitrogen atmosphere. When the element was driven with a current density of 11 mA/cm$^2$, a light emission luminance of 900 cd/m$^2$ was achieved. The emitted light was white. The luminance half-life when the element was driven with a current density of 110 mA/cm$^2$ was approximately 100 hours.

(Evaluation of White Color Emission)

The result of evaluation of the white color emission from the element created in the example 3-1 will now be described. In a white light emitting element as shown in example 3-1 in which the compound represented by the chemical formula (36) was doped to the hole transport layer with TPTE as the primary constituent and in which DPVBi was used in the emissive layer, the measurement result of the chromaticity coordinates were X=0.33 and Y=0.33, which indicates the approximate center of the white color region.

On the other hand, the chromaticity coordinates of the light emission color of the DPVBi alone were X=0.16 and Y=0.21. The chromaticity coordinates for the light emission color of the compound represented by the chemical formula (36) were X=0.51 and Y=0.46. From these results, it can be seen that the chromaticity coordinates of the light emission color of the white light emitting element obtained by combining these light emission colors were on a line segment which linearly connects respective chromaticity coordinates of the two materials when used alone. Moreover, the white light emission obtained by combining two materials such as in the example 3-1 changes depending on the doping concentration of the quinoline derivative compound represented by the chemical formula (36), thickness of the doped hole transport layer, and the thickness of the blue emissive layer.

Therefore, in the white color light emitting element according to the preferred embodiments of the present invention, the chromaticity coordinates of "white" can be adjusted to desired values by adjusting these conditions, that is, the doping concentration, thickness, material for the hole transport layer, etc.

Another factor which changes chromaticity coordinate values is the material for the hole transport layer. The chromaticity coordinates when the quinoline derivative compound represented by the chemical formula (36) was doped to the hole transport material TPTE used in the example 3-1 were equal to the chromaticity coordinates X=0.51 and Y=0.46 of the compound represented by the chemical formula (36) alone. In contrast, when α-NPD was used as the hole transport layer and the compound represented by the chemical formula (36) was doped into the hole transport layer, the chromaticity coordinates became X=0.59 and Y=0.40, and, thus, there is a tendency that red becomes more intense. As described, the light emission color also changes depending on the composition of the material which is the primary constituent of the hole transport layer. The element structure when α-NPD was used as the primary constituent of the hole transport layer was identical to that in the example 3-1 except for the material.

(Advantage of Invention)

According to the present invention, a novel quinoline derivative compound can be obtained in which at least two of substituents $R_1$~$R_7$ in a compound represented by a general chemical formula (1) are substituted by a substituent represented by the chemical formula (2).

Because this quinoline derivative has a molecular structure such that the conjugate system is long, light emission with high luminance and of yellow red range is possible. Also, the quinoline derivative is chemically stable. Therefore, by employing this new material, for example, as a material having a light emission function (material for the emissive layer or material to be doped to the emissive layer) in an organic EL element, it is possible to realize an organic EL element having high luminance, high light emitting efficiency, and long life time.

Not only does the quinoline derivative of the present invention emit light in the yellow~red range when used alone, but the quinoline derivative also produces light in similar wavelength regions in a hole transport layer when doped to the hole transport layer. Therefore, by doping the quinoline derivative to the hole transport layer of an organic EL element, light can be emitted having a color synthesized from the light from the emissive layer and the light from the hole transport layer. For example, by employing a blue light emitting material in the emissive layer and employing the quinoline derivative compound of the present invention as the doping material to the hole transport layer, it is possible to obtain an organic EL element having a white light emission characteristic through synthesis of the blue light from the blue emissive layer and the light in the orange~red range from the hole transport layer. In such a case, a synthesis color with the light from the emissive layer can be achieved by simply doping the hole transport layer, and thus there is no need to separately provide an additional emissive layer.

Moreover, it is possible to further improve the light emission efficiency, stability, or the like by introducing a desired functional group to the substituent in the compound of the present invention such as, for example, introducing an electron attracting susbtituent in the substituent other than the substituents $R_1$~$R_7$ of chemical formula (1) substituted by the substituent represented by the chemical formula (2).

Industrial Applicability

The organic compound according to the present invention is suited as a light emitting material, for example, for a light emitting material of an organic electroluminescence element and material for other electronic devices.

What is claimed is:

1. A quinoline derivative compound represented by the following general chemical formula (1),

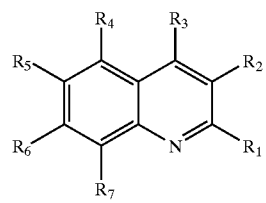

(1)

wherein groups represented by the following chemical formula (2) are introduced to at least two of the substituents $R_1$–$R_7$ in the chemical formula (1),

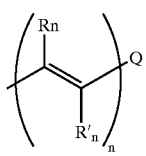

(2)

the number n of double bonds is 2 or greater in at least one of the introduced groups represented by the chemical formula (2);

Q in the chemical formula (2) is an aromatic group having carbon or a heteroatom in the skeleton of the ring; and substituents $R_n$ and $R'_n$ in the chemical formula (2) are independent functional groups which are identical or different, or the substituents $R_n$ and $R'_n$ are cyclized by a saturated bond with each other or with an adjacent group.

2. An organic compound according to claim 1, wherein at least one of the substituents $R_1$–$R_7$ in the chemical formula (1) other than the substituents represented by the chemical formula (2) is an electron attracting substituent.

3. An organic compound according to claim 2, wherein the aromatic group Q in the chemical formula (2) has at least one of the substituents $R_Q$; and at least one of the substituents $R_Q$ is an electron donating substituent.

4. An organic compound according to claim 3, wherein the substituent $R_3$ in the chemical formula (1) is an electron attracting substituent and the substituent Q in the chemical formula (2) is an electron donating substituent.

5. An organic compound according to claim 4, wherein the substituent $R_3$ in the chemical formula (1) is a cyano group and the substituent Q in the chemical formula (2) is a p-aminophenyl group.

6. An organic electroluminescence element in which an organic compound layer including an emissive layer is formed between two electrodes, wherein the organic compound layer includes an organic compound according to claim 5.

7. An organic electroluminescence element according to claim 6, wherein the organic compound layer comprises a hole transport layer and an emissive layer, and the organic compound is doped to the hole transport layer.

8. An organic electroluminescence element in which an organic compound layer including an emissive layer is formed between two electrodes, wherein the organic compound layer comprises a blue light emitting layer and a hole transport layer into which an organic compound according to claim 5 is doped, and the organic electroluminescent element emits white light.

9. An organic compound according to claim 3, wherein the number n of the double bonds is 2 or greater in all of the introduced sub stituents represented by the chemical formula (2).

10. An organic compound according to claim 9, wherein the number n of the double bonds is 5 or less in at least one of the introduced substituents represented by the chemical formula (2).

11. An organic compound according to claim 9, wherein the substituent $R_3$ in the chemical formula (1) is a cyano group and the substituent Q in the chemical formula (2) is a p-aminophenyl group.

12. An organic electroluminescent element in which an organic compound layer including an emissive layer is formed between two electrodes, wherein the organic compound layer includes an organic compound according to claim 11.

13. An organic electroluminescence element according to claim 12, wherein the organic compound layer comprises a hole transport layer and an emissive layer, and the organic compound is doped to the hole transport layer.

14. An organic electroluminescence element in which an organic compound layer including an emissive layer is formed between two electrodes, wherein the organic compound layer comprises a blue light emitting layer and a hole transport layer into which an organic compound according to claim 11 is doped, and the organic electroluminescence element emits white light.

15. An organic compound according to claim 9 wherein the number n of the double bonds is 3 or less in the substituents represented by the chemical formula (2).

16. An organic compound according to claim 15, wherein the substituent $R_3$ in the chemical formula (1) is a cyano group and the substituent Q in the chemical formula (2) is a p-aminophenyl group.

17. An organic electroluminescence element in which an organic compound layer including an emissive layer is formed between two electrodes, wherein the organic compound layer includes an organic compound according to claim 16.

18. An organic electroluminescence element according to claim 17, wherein the organic compound layer comprises a hole transport layer and an emissive layer, and the organic compound is doped to the hole transport layer.

19. An organic electroluminescence element in which an organic compound layer including an emissive layer is formed between two electrodes, wherein the organic compound layer comprises a blue light emitting layer and a hole transport layer into which an organic compound according to claim 16 is doped, and the organic electroluminescence element emits white light.

20. An organic electroluminescence element in which an organic compound layer including an emissive layer is formed between two electrodes, wherein the organic compound layer includes an organic compound according to claim 9.

21. An organic electroluminescence element according to claim 20, wherein the organic compound layer comprises a hole transport layer and an emissive layer, and the organic compound is doped to the hole transport layer.

22. An organic electroluminescence element in which an organic compound layer including an emissive layer is formed between two electrodes, wherein the organic compound layer comprises a blue light emitting layer and a hole transport layer into which an organic compound according to claim 9 is doped, and the organic electroluminescence element emits white light.

\* \* \* \* \*